United States Patent [19]

Haber et al.

[11] Patent Number: 5,342,389
[45] Date of Patent: Aug. 30, 1994

[54] TISSUE MANIPULATOR

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 874,934

[22] Filed: Apr. 28, 1992

[51] Int. Cl.⁵ .............................................. A61B 17/28
[52] U.S. Cl. ...................................... 606/205; 606/148
[58] Field of Search .................. 606/51, 52, 83, 167, 606/170, 174, 144, 142, 205–210, 139, 140, 147, 148; 128/750–755, 3, 4, 6; 30/137; 294/99.2, 115

[56] References Cited

U.S. PATENT DOCUMENTS

| | | |
|---|---|---|
| 1,274,669 | 8/1918 | Bohn . |
| 2,363,334 | 11/1944 | Jones . |
| 2,365,647 | 12/1944 | Ogburn . |
| 2,670,519 | 3/1954 | Recklitis .............................. 606/206 |
| 3,168,097 | 2/1965 | Dormia . |
| 3,687,138 | 8/1972 | Jarvik ................................. 606/139 |
| 4,393,872 | 7/1983 | Reznik et al. ...................... 606/206 |
| 4,427,014 | 1/1984 | Bel et al. ........................... 128/751 |
| 4,580,567 | 4/1986 | Schweitzer et al. . |
| 4,607,620 | 8/1986 | Storz ................................. 606/206 |
| 4,643,190 | 2/1987 | Heimberger . |
| 4,815,476 | 3/1989 | Clossick . |
| 4,872,456 | 10/1989 | Hasson . |
| 4,881,550 | 11/1989 | Kothe ................................. 128/752 |
| 4,890,615 | 1/1990 | Caspari et al. . |
| 5,084,054 | 1/1992 | Bencini et al. . |
| 5,144,961 | 9/1992 | Chen et al. ......................... 606/139 |
| 5,156,608 | 10/1992 | Troidl et al. ....................... 606/142 |
| 5,222,962 | 6/1993 | Burkhart ............................ 606/148 |

OTHER PUBLICATIONS

Jarit Laparoscopic Cholecystectomy Instruments, Star 2000 Series, 1991.

Primary Examiner—Stephen C. Pellegrino
Assistant Examiner—Wm. Lewis
Attorney, Agent, or Firm—Townsend and Townsend Khourie and Crew

[57] ABSTRACT

An endoscopic tissue manipulator (2) has jaw surfaces (20, 22) with peaks (24) and troughs (26) which engage when the jaws (10, 12) are closed. The jaw surfaces have no sharp edges and have a gap (75) therebetween when the jaws are closed to minimize damage to tissue (76, 78). A pursestring suture can be quickly made by passing a suture-material-carrying needle (86) along axial grooves (100, 102) formed in the jaw surfaces while the jaws are closed and holding tissue therebetween. The needle is then removed leaving the suture material in the tissue. The suture material is then tied off creating the pursestring-type suture. The jaws manipulate the compliant tissue in a single movement to create multiple folds of the tissue which can be pierced by the suture-material carrying needle in a single stroke.

25 Claims, 7 Drawing Sheets

TISSUE MANIPULATOR

BACKGROUND OF THE INVENTION

Endoscopic tissue manipulators, such as grasping and extracting forceps, are well known. One of the challenges of designing these instruments is to securely hold the tissue while avoiding damage to the tissue. Some of the difficulties encountered when working endoscopically are that the work space is considerably smaller than with more traditional open surgical procedures. As a result, grasping tissue can be more difficult to accomplish.

Additionally, because of the nature of the working space, once tissue is damaged due to grasping, the damage may be more difficult to detect and correct. The operator often finds it harder to visualize and to manipulate tissue when working endoscopically.

Moreover, when tissue is grasped through an endoscopic device, the grasp can be very tenuous and involve a very small amount of tissue. The operator may need to make do with this situation as he may not be able to get a better grasp of the tissue or a better field of visualization. Even in traditional open surgical procedures, this problem of grasping tissue without causing damage persists.

For example, in many vascular procedures, the grasping device or forceps is modified to attempt to minimize damage to fragile blood vessels. One way of accomplishing this is to use "shod" clamps. This refers to the practice of placing a material, usually a short length of tubular fabric or elastomer, on the grasping portions of the clamp. This solution is not completely satisfactory because the tubular material tends to slip off the clamps. Additionally, with shod devices, the tubular material may prevent a sufficient grasp of the tissue. In summary, there are competing requirements in designing a device to grasp tissue. That is, the device must grasp the tissue sufficiently for whatever further manipulation is required as well as avoid damage to the tissue as much as is feasible.

Another challenge for physicians during endoscopic procedures involves suturing tissue, typically to close an incision. Conventional sutures require each individual stitch to be tied separately, a tedious task under even the best of conditions. Certain specialty suture techniques do not always require tying of each individual stitch, but they may have other considerations which render the technique difficult or time-consuming.

For example, a purse-string suture may be placed by pushing a needle carrying suture material through successive folds of tissue. This is typically done in an annular pattern and the suture is tightened by pulling the two ends. Thus, the tissue is drawn together in a fashion reminiscent of a purse string. The two ends of the suture may be secured, typically by tying them together or perhaps knotting off an end. The purse string technique is fairly time-consuming because each individual fold of tissue must be arranged by the surgeon and then the needle is pushed through. Also, it is tedious to arrange the folds symmetrically and evenly. The problems are amplified when the surgery is carried out in a small space or with a small field of visualization, such as with endoscopic techniques.

SUMMARY OF THE INVENTION

The present invention is directed to an endoscopic tissue manipulator which permits tissue to be securely held between the opposed jaw surfaces of the manipulator without damage to the tissue; this ability is based upon the novel configuration of the surfaces and the design of the jaws which ensures a minimum gap is maintained between the jaw surfaces when the jaws are closed. In addition, the configuration of the jaw surfaces is such that the manipulator can be adapted to permit a suture carrying needle to be passed longitudinally between the jaw surfaces with the tissue captured therebetween to create a pursestring type of suture.

The tissue manipulator includes jaws having opposed complementarily shaped surfaces with troughs and peaks. The jaw surfaces are configured so that peaks and troughs mesh when the jaws are in the closed position. When the jaws are closed the peaks on the jaws enter into the troughs of the other jaws. Tissue captured between the jaw surfaces is placed in a folded tissue configuration with the tissue in what can be described as undulating, accordion-like or generally S-shaped.

The tissue manipulator can be adapted to act as a pursestring type of suturing device. This is achieved in the preferred embodiment by forming aligned, axially extending grooves along the opposed jaw surfaces. The grooves are sized to permit the proximal end of a suture-carrying needle to pass through the grooves when the jaws are in the closed position. Doing so permits the needle to repeatedly pass through the surfaces of the folds of tissue held in the accordion-like configuration. The needle is then removed from the tissue while the suture material is prevented from being pulled back through the tissue. The suture material is then tied off and the jaws are opened to create a pursestring type of suture.

Other features and advantages of the invention will appear from the following description in which the preferred embodiment has been set forth in detail in conjunction with the accompanying drawings.

DESCRIPTION OF THE PREFERRED EMBODIMENT

Figure 1:
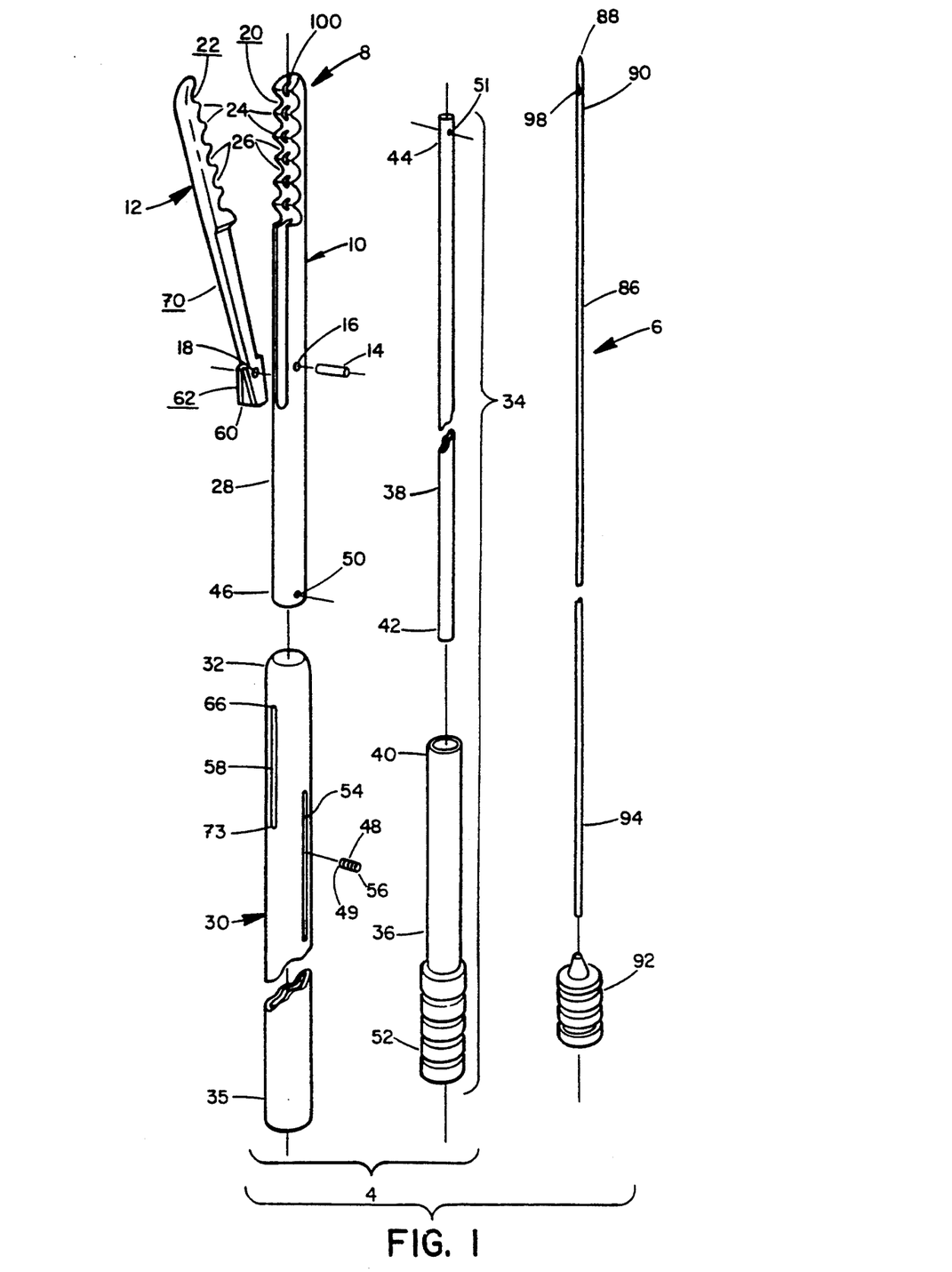
FIG. 1 is an exploded isometric view of an endoscopic device made according to the invention.

FIG. 1 illustrates an endoscopic device 2 including a tissue manipulator 4 and a needle assembly 6. Tissue manipulator 4 includes a jaw assembly 8 including a fixed jaw 10 to which an articulating jaw 12 is pivotally mounted by passage of a pivot pin 14 through holes 16, 18 formed in fixed and articulating jaws 10, 12, respectively. Jaws 10, 12 have opposed jaw surfaces 20, 22 with complementarily sized and positioned peaks 24 and troughs 26 formed therein. The surfaces 20, 22 are sized and configured to securely grasp tissue while minimizing tissue damage, as will be discussed below.

Figure 2:
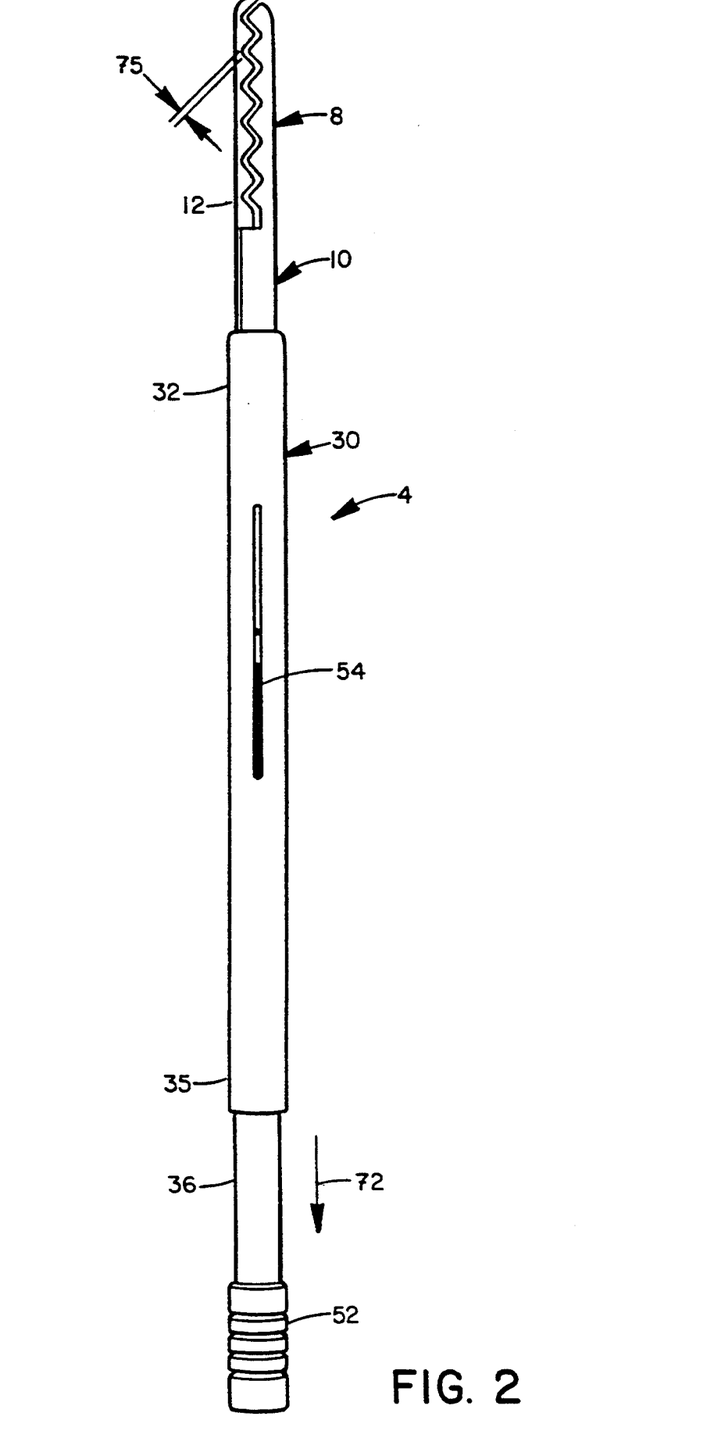
FIG. 2 is an assembled side view of the tissue manipulator portion of the endoscopic device of FIG. 1 with the jaws in the closed position.
Figure 2A:
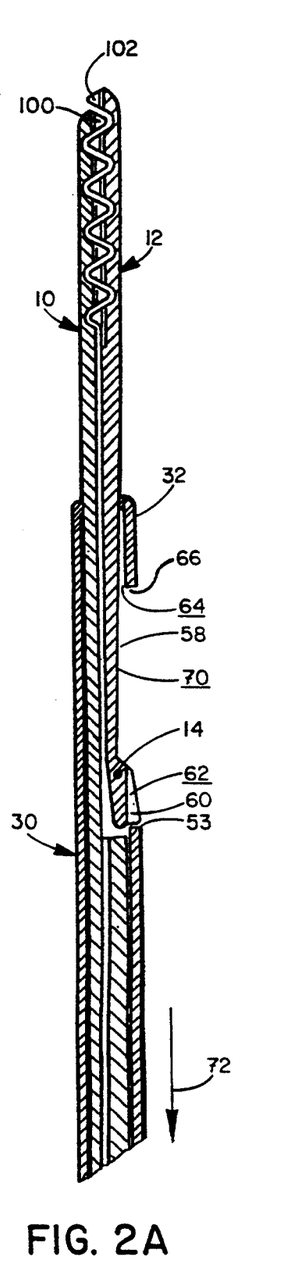
FIG. 2A is an enlarged cross-sectional view of the distal end of the tissue manipulator of FIG. 2.
Figure 3:
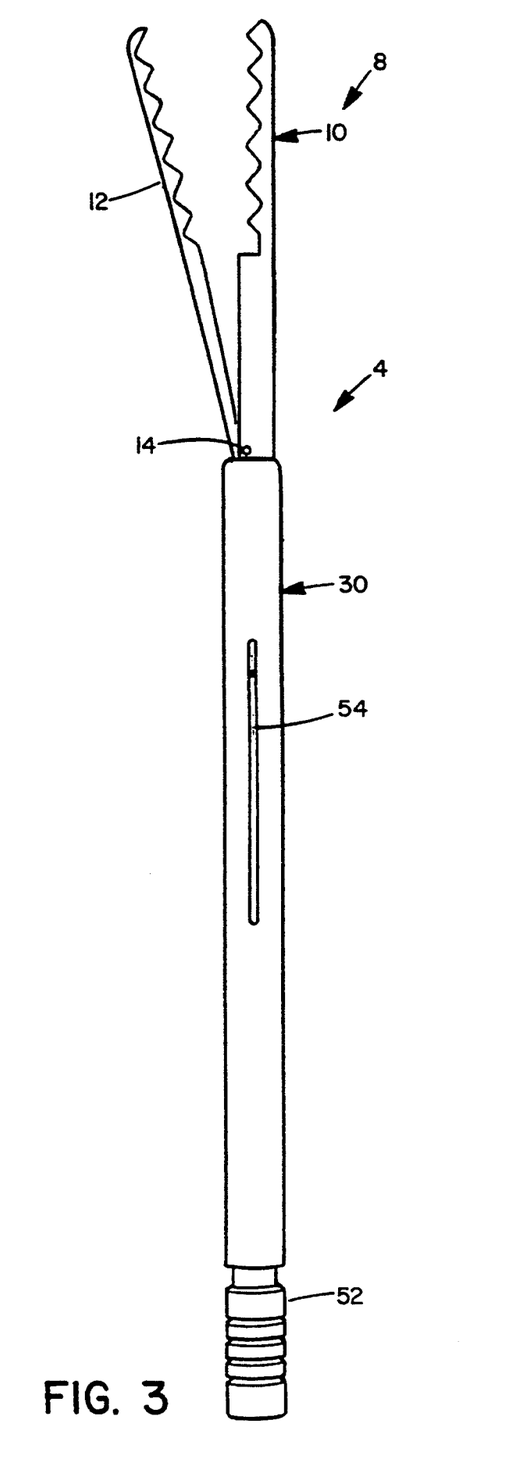
FIG. 3 illustrates the tissue manipulator of FIG. 2 with the jaws in the open position.
Figure 3A:
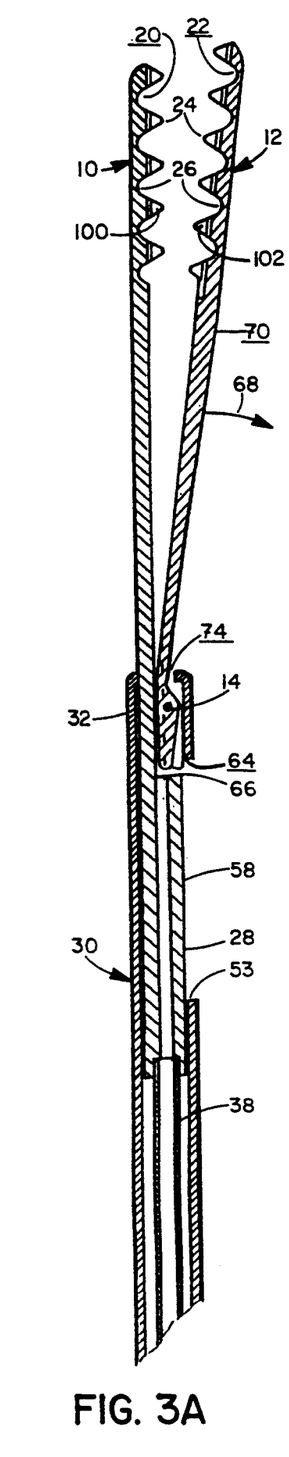
FIG. 3A is an enlarged cross-sectional view of the distal end of the tissue manipulator of FIG. 3.

The proximal end of 28 of jaw assembly 8 is housed within a tubular body 30 and extends from the distal end 32 of the tubular body as shown in FIG. 2. Jaw assembly 8 is moved axially within tubular body 30 by the manipulation of a drive tube assembly 34 which extends from the proximal end 35 of tubular body 30. Drive tube assembly 34 includes a drive tube 36 and a connecting tube 38 secured to one another at their opposed ends 40, 42 through a press fit. The distal end 44 of connecting tube 38 passes through the proximal end 46 of fixed jaw 10. Drive tube assembly 34 is secured to jaw assembly 8 through the use of a threaded limit pin 48. Limit pin 48 passes through a threaded hole 50 formed in proximal end 28 of fixed jaw 10. Limit pin 48 is preferably a set screw and is threaded into hole 50 until the tip 49 of pin 48 engages a blind hole or depression 51 formed at distal end 44 of connecting tube 38. This secures jaw assembly 8 to drive tube assembly 34 so that jaw assembly 8 can be moved between the closed position of FIGS. 2 and 2A and the open position of FIGS. 3 and 3A by grasping drive handle 52 and pulling or pushing on the drive handle.

Tubular body 30 has an axially extending travel limit slot 54 formed therein. Pin 48 is sized so that the head 56 of the pin is situated within slot 54. Thus, threaded limit pin 48 not only connects drive tube assembly 34 to jaw assembly 8, pin 48 also limits the reciprocal axial movement of the combined drive tube assembly and jaw assembly by the engagement of the limit pin with the ends of slot 54.

Tubular body 30 also includes a clearance slot 58 towards distal end 32 oriented about 90° from slot 54. Articulating jaw 12 has a wedged-shaped member 60 positioned adjacent hole 18. Member 60 has a width sized to pass through slot 58. Member 60 has an opening ramp surface 62 which engages an internal opening cam surface 64 adjacent distal end 66 of slot 58. Doing so pivots articulating jaw 12 in the direction of arrow 68 so jaw assembly 8 moves from the closed position of FIG. 2A to the open position of FIG. 3A. Articulating jaw 12 has a closing ramp surface 70 which, as drive handle 52 is pulled in the direction of arrow 72, is engaged by a closing cam surface 74 at distal end 32 of tubular body 30. The relatively long length of closing ramp surface 70 allows the user to exert an adequate closing force on jaws 10, 12. Axial movement of jaw assembly 8 in the direction of arrow 72 is halted by the engagement of member 60 with the proximal end 73 of slots 58.

Figure 2B:
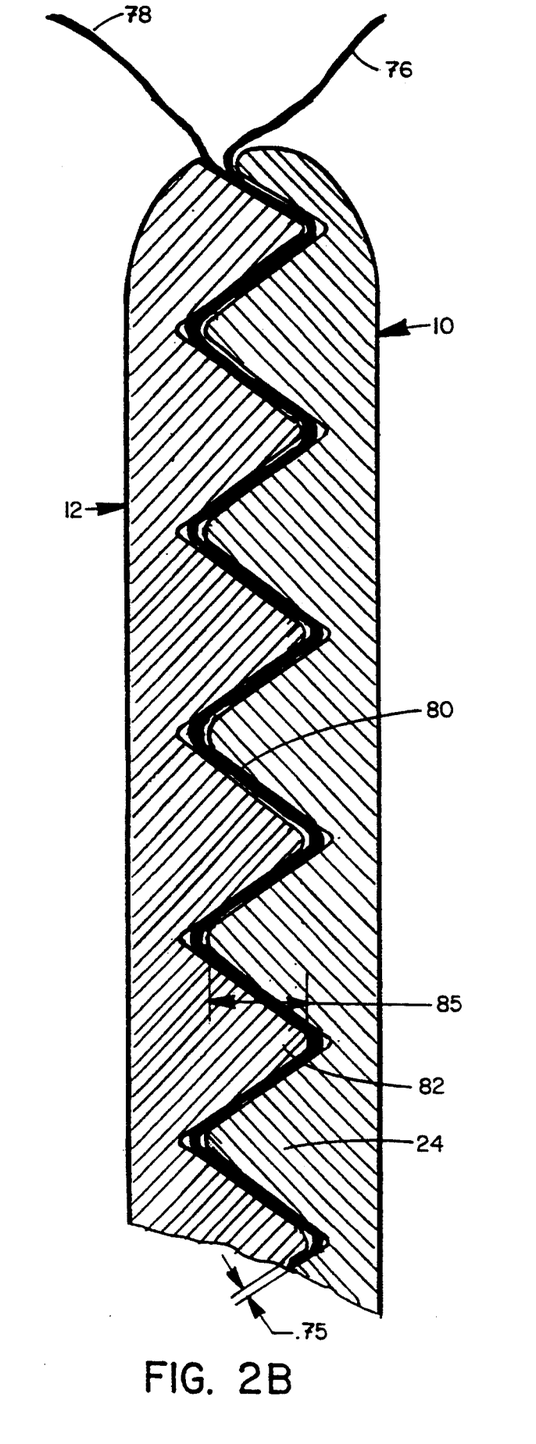
FIG. 2B is a view similar to FIG. 2A but with tissue between the jaw surfaces.

FIG. 2 shows the provision of a generally constant gap 75 between jaw surfaces 20, 22. Gap 75 is present when jaws 10, 12 are completely closed to help prevent damage to layers of tissue 76, 78, shown in FIG. 2B, when the tissue is grasped by jaws 10, 12. Gap 75 in the preferred embodiment is sized for manipulation of human tissue (typically about 0.050 inch (1.2 mm) thick) and is about 0.070 inch (1.8 mm) to 0.080 inch (2.0 mm) wide. Another feature of jaw surfaces 20, 22 which helps to prevent tissue damage is the elimination of sharp corners along those portions of surfaces 20, 22 which touch tissue 76, 78. In particular, the minimum radius of curvature for peaks 24 is 0.050 inch (1.2 mm). Other dimensions can be used according to the characteristics of the tissue being manipulated. The gentle grasping of tissue 76, 78 is shown in FIG. 2B. The provision of gap 75 when jaws 10, 12 are fully closed and the use of flat or rounded surfaces abutting tissue 76, 78 help the prevent tissues damage.

How securely jaws 10, 12 engage tissue 76, 78 depends partly upon the size of gap 75 relative to the thickness of tissue 76, 78. However, the amount of holding force exerted by jaws 10, 12 depends largely upon jaw 10, 12 forming tissue 76, 78 into convoluted, generally S-shaped or accordion-like folds 80 of tissue 76, 78. That is, the tips 82, 84 of peaks 24 for jaws 10, 12 engage the respective troughs 26 of jaws 12, 10 sufficiently to create an overlap 85. Overlap 85 is preferably equal to about 2 to 5 times the size of gap 75. In the preferred embodiment, overlap 85 is about 0.24 inch (6.1 mm), or thus about 3 times the size of gap 75. In addition to ensuring that tissue 76, 78 is securely but gently held between jaws 10, 12, the degree of overlap 85 is also sized to be greater than the diameter of the needle used when creating a pursestring type of suture as is discussed below.

Figure 4:
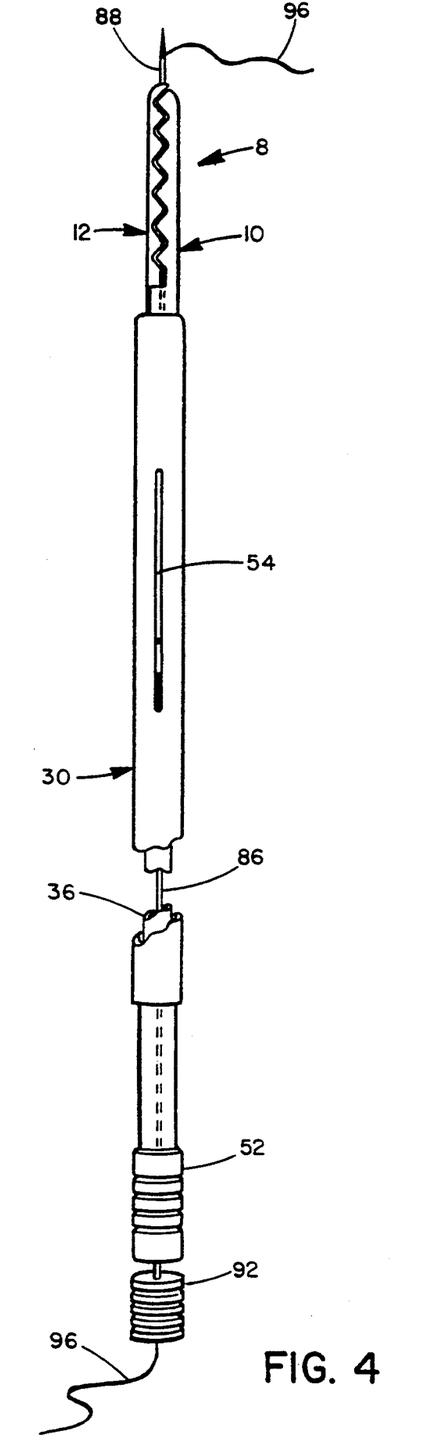
FIG. 4 is an assembled side view of the endoscopic device of FIG. 1 with portions broken away to show the coaxial assembly of the needle, drive tube and tubular body.
Figure 4A:
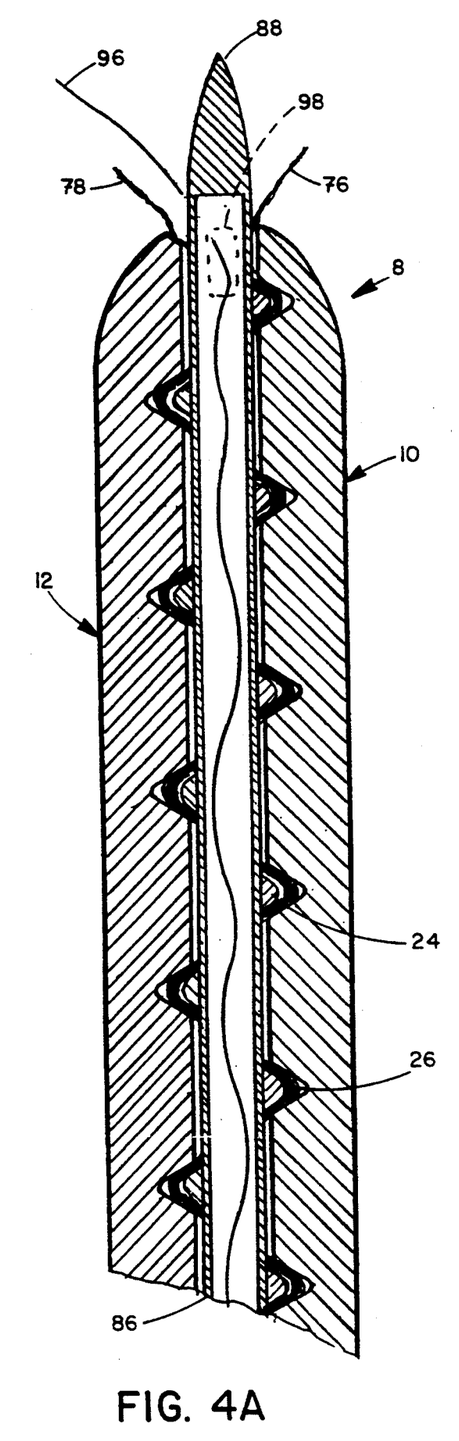
FIG. 4A is an enlarged cross-sectional view of the endoscopic device of FIG. 4 showing the passage of a length of suture material along the center of the hollow needle and out the suture exit hole in the needle adjacent the needle point, the needle passing through accordion-like folds of tissue.
Figure 4B:
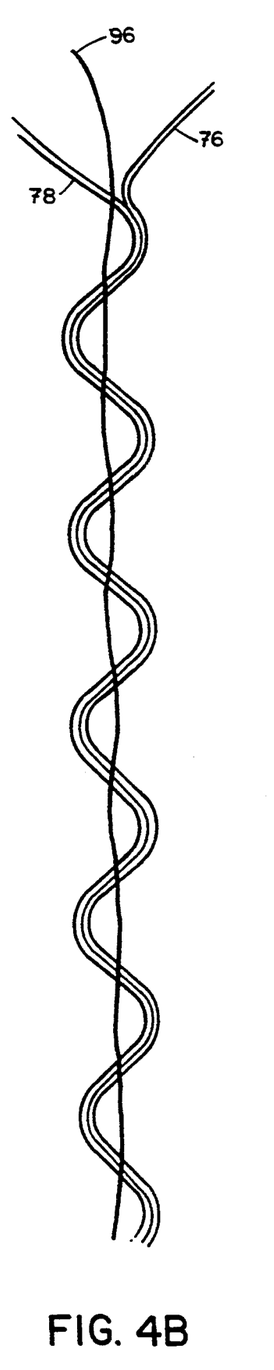
FIG. 4B illustrates the tissue and suture material of FIG. 4A after the needle has been removed, the jaws of the tissue manipulator have been opened and the suture material has been tied off to create a pursestring-type of suture.

Needle assembly 6 includes an elongate hollow needle 86 having a point 88 at a distal end 90 thereof and a hollow needle handle 92 mounted to the proximal end 94 of needle 86 using a press fit. A length of suture material 96 passes through hollow needle handle 92, along the interior of hollow needle 86 and out through a suture exit hole 98 at distal end 90. Surfaces 20, 22 have axially extending grooves 100, 102 formed therein. Grooves 100, 102 are sized to accept the distal end 90 of needle 86 when jaws 20, 22 are in the closed position of FIG. 2B. In this way, once tissue 76, 78 has been capture between jaws 10, 12, needle 86, together with suture material 96, can be inserted through drive tube assembly 34, through hollow proximal end 28 of fixed jaw 10, between fixed jaws 10, 12 and finally along grooves 100, 102 as suggested in FIG. 4A. By making the diameter of needle 86 smaller than distance 85 allows needle 86 to pass through accordion-like folds 80 of tissue 76, 78. The user then pulls needle 86 out from tissue manipulator 4 by grasping and pulling on handle 92 in the direction of arrow 72 while holding the distal end of suture material 96 to keep the suture material from pulling back through tissue 76, 78. Jaws 10, 12 are then released and suture material 96 is tied off in a conventional manner to complete the pursestring type of suture as shown in FIG. 4B.

Modifications and variations can be made to this disclosed embodiment without departing from the subject of the invention as defined in the following claims. Although endoscopic device 2 is preferably made of stainless steel, other biologically compatible materials can be used as well. Jaw assembly 8 has only one articulating jaw; if desired, tissue manipulator 4 could be made with two movable jaws. Other types of drivers for opening and closing jaws 8, 10 could be used as well. Suture material 96 need not pass through the interior of needle 86; needle 86 need not be hollow or have a round cross-sectional shape. Additionally, the device could be modified for non-endoscopic use in open surgical procedures. The tissue manipulator may be especially useful as a forceps or grasping instrument in vascular procedures because blood vessels tend to be fragile and susceptible to instrument damage from crushing.

What is claimed is:

1. An endoscopic tissue manipulator comprising:
   an elongate body having a distal end, a proximal end, and a longitudinal axis;
   first and second jaws at the distal end of the body, said jaws having opposed jaw surfaces, said jaws being movable between open and closed positions, the first jaw being pivotally mounted to the second jaw at a pivot point;
   a jaw driver operably coupled to the jaws and including a jaw driver element at the proximal end of the body which can be actuated by a user to move the jaws between the open and closed positions;
   the opposed jaw surfaces having troughs and peaks arranged along said longitudinal axis, said jaw surfaces configured so that one or more peaks of said jaw surfaces are at least partially housed within corresponding troughs of said jaw surfaces when said jaws are in the closed position;
   said jaw surfaces defining a gap therebetween when said jaws are in the closed position, said gap sized so to minimize damage to tissue captured between the jaw surfaces; and
   said jaw surfaces having portions which contact the tissue, said portions having curved surface portions with a minimum radius of curvature chosen to minimize tissue damage, the jaw surfaces being complementary-shaped surfaces; the jaw driver including an elongate drive connector connecting the jaw driver element and the second jaw.

2. The tissue manipulator of claim 1 wherein the gap is about 2 mm.

3. The tissue manipulator of claim 1 wherein the minimum radius of curvature is about 1.2 mm.

4. The tissue manipulator of claim 1 further comprising means for creating accordion-like folds of said tissue between the jaw surfaces when the jaws are in the closed position.

5. An endoscopic tissue manipulator comprising:
   an elongate body having a distal end and a proximal end;
   first and second jaws at the distal end of the body, said jaws having opposed jaw surfaces, said jaws being movable between open and closed positions, the first jaw being pivotally mounted to the second jaw at a pivot point, the first jaw having an opening ramp surface and a closing ramp surface;
   a jaw driver operably coupled to the jaws and including a jaw driver element at the proximal end of the body which can be actuated by a user to move the jaws between the open and closed positions, the jaw driver including an elongate drive connector connecting the jaw driver element and the second jaw;
   the opposed jaw surfaces having troughs and peaks, said jaw surfaces configured so that one or more peaks of said jaw surfaces are at least partially housed within corresponding troughs of said jaw surfaces when said jaws are in the closed position;
   said jaw surfaces defining a gap therebetween when said jaws are in the closed position, said gap sized so to minimize damage to tissue captured between the jaw surfaces, said jaw surfaces being complementary-shaped surfaces; and
   said jaw surfaces having portions which contact the tissue, said portions having curved surface portions with a minimum radius of curvature chosen to minimize tissue damage.

6. The tissue manipulator of claim 5 wherein the opening ramp surface is on a first side of the pivot point and the closing ramp surface is on a second side of the pivot point.

7. The tissue manipulator of claim 5 wherein manipulation of the jaw driver elements causes portions of the first and second jaws to move longitudinally within a portion of the tubular body.

8. The tissue manipulator of claim 7 wherein the tubular body has first and second surfaces which engage the opening and closing ramp surfaces causing the jaws to move between the open and closed positions when the jaw driver element is actuated.

9. An endoscopic tissue manipulator comprising:
   an elongate body having a distal end and a proximal end;
   first and second jaws at the distal end of the body, said jaws having opposed jaw surfaces, said jaws being movable between open and closed positions;
   a jaw driver operably coupled to the jaws and including a jaw driver element at the proximal end of the body which can be actuated by a user to move the jaws between the open and closed positions;
   the opposed jaw surfaces having troughs and peaks, said jaw surfaces configured so that one or more peaks of said jaw surfaces are at least partially housed within corresponding troughs of said jaw surfaces when said jaws are in the closed position;
   said jaw surfaces defining a gap therebetween when said jaws are in the closed position, said gap sized so to minimize damage to tissue captured between the jaw surfaces;
   said jaw surfaces having portions which contact the tissue, said portions having curved surface portions with a minimum radius of curvature chosen to minimize tissue damage;
   means for creating accordion-like folds of said tissue between the jaw surfaces when the jaws are in the closed position;
   an elongate suturing needle having a point and adapted to carry a length of suture material from a position adjacent the point; and
   means for movably guiding the needle along the elongate body and between the jaws when the jaws are in the closed position so to allow the needle to be driven through the folds of tissue so that a purse-string type of suture can be made.

10. An endoscopic tissue manipulator comprising:
    an elongate body having a distal end and a proximal end;
    first and second jaws at the distal end of the body, said jaws having opposed jaw surfaces, said jaws being movable between open and closed positions;
    a jaw driver operably coupled to the jaws and including a jaw driver element at the proximal end of the body which can be actuated by a user to move the jaws between the open and closed positions;
    the opposed jaw surfaces having troughs and peaks, said jaw surfaces configured so that one or more peaks of said jaw surfaces are at least partially housed within corresponding troughs of said jaw surfaces when said jaws are in the closed position;

said jaw surfaces defining a gap therebetween when said jaws are in the closed position, said gap sized so to minimize damage to tissue captured between the jaw surfaces;

said jaw surfaces having portions which contact the tissue, said portions having curved surface portions with a minimum radius of curvature chosen to minimize tissue damage;

a suturing needle having a point at a distal end thereof, a handle at a proximal end thereof and a suture exit adjacent the point, said needle adapted to carry a length of suture material along the length of the needle with the distal end of the length of suture material extending past the suture exit;

the needle having a lateral dimension less than the lateral distance between two adjacent peaks on the first and second jaws when the jaws are in the closed position;

the jaw surfaces each including an axially extending groove formed therein, the grooves sized to accept the proximal end of the needle when the jaws are in the closed position; and the needle being mountable to the body for reciprocal movement along a distal/proximal path between a retracted position, with the needle point located between the proximal end of the body and the axial groove, and an extended position, with the needle housed within said axial groove;

whereby movement of the needle from the retracted position to the extended position after the tissue has been captured between the jaw surfaces with the jaws in the closed position causes the needle and the length of suture material therewith to pass through the tissue, whereupon movement of the needle from the extended position to the retracted position while preventing the distal end of the suture material from pulling back through the tissue create a pursestring type of suture in the tissue.

11. The tissue manipulator of claim 10 wherein the needle has a hollow interior and the suture exit defines a pathway from the hollow interior to a region external of the needle.

12. The tissue manipulator of claim 10 wherein the needle has a circular cross-sectional shape.

13. The tissue manipulator of claim 10 wherein the body is tubular with a hollow interior and the needle passes through said hollow interior.

14. The tissue manipulator of claim 10 wherein the jaw surfaces are sized and configured to create a plurality of accordion-like folds in the tissue to permit the needle to pass through the accordion-like folds of the tissue.

15. An improved endoscopic tissue manipulator of the type having user-manipulatable first and second jaws movable between open and closed positions, the improvement comprising:

an elongate body having a distal end, a proximal end, and a longitudinal axis;

the jaws having opposed jaw surfaces, the opposed jaw surfaces being surfaces with troughs and peaks, said jaw surfaces configured so that one or more peaks of said jaw surfaces nest within one or more troughs of the opposed jaw surfaces when the jaws are in the closed position, said first jaw being pivotally coupled to said second jaw;

means for slidably coupling the second jaw to the elongate body for movement in a direction of said longitudinal axis;

said jaw surfaces defining a gap therebetween when said jaws are in the closed position, said gap sized so to minimize damage to tissue captured between the jaw surfaces; and said jaw surfaces having portions which contact the tissue, said portions having curved surface portions with a minimum radius of curvature chosen to minimize tissue damage when the jaws are in the closed position.

16. The improved tissue manipulator of claim 15 wherein said jaw surfaces are complementarily shaped surfaces and are configured to create a plurality of accordion-like folds of said tissue.

17. The improved tissue manipulator of claim 15 wherein the opposed jaw surfaces have no sharp tissue-engaging corners to minimize tissue damage.

18. An improved endoscopic tissue manipulator of the type having user-manipulatable jaws movable between open and closed positions, the improvement comprising:

the jaws having opposed jaw surfaces, the opposed jaw surfaces being surfaces with troughs and peaks, said jaw surfaces configured so that one or more peaks of said jaw surfaces nest within one or more troughs of the opposed jaw surfaces when the jaws are in the closed position, the opposed jaw surfaces having peaks with rounded tips;

said jaw surfaces defining a gap therebetween when said jaws are in the closed position, said gap sized so to minimize damage to tissue captured between the jaw surfaces; and said jaw surfaces having portions which contact the tissue, said portions having curved surface portions with a minimum radius of curvature chosen to minimize tissue damage when the jaws are in the closed position.

19. The improved tissue manipulator of claim 18 wherein the minimum radii of curvature of the rounded tips is about 1.2 mm.

20. An improved endoscopic tissue manipulator of the type having user-manipulatable jaws movable between open and closed positions, the improvement comprising:

the jaws having opposed jaw surfaces, the opposed jaw surfaces being surfaces with troughs and peaks, said jaw surfaces configured so that one or more peaks of said jaw surfaces nest within one or more troughs of the opposed jaw surfaces when the jaws are in the closed position, said jaw surfaces being complementarily shaped surfaces and being configured to create a plurality of accordion-like folds of said tissue;

said jaw surfaces defining a gap therebetween when said jaws are in the closed position, said gap sized so to minimize damage to tissue captured between the jaw surfaces; and said jaw surfaces having portions which contact the tissue, said portions having curved surface portions with a minimum radius of curvature chosen to minimize tissue damage when the jaws are in the closed position;

an elongate suturing needle having a point and adapted to carry a length of suture material from a position adjacent the point; and means for movably guiding the needle along the elongate body and between the jaws when the jaws are in the closed position so to allow the needle to be driven through the folds of tissue so that a pursestring type of suture can be made.

21. An improved endoscopic tissue manipulator of the type having user-manipulatable jaws movable between open and closed positions, the improvement comprising:
   the jaws having opposed jaw surfaces, the opposed jaw surfaces being surfaces with troughs and peaks, said jaw surfaces configured so that one or more peaks of said jaw surfaces nest within one or more troughs of the opposed jaw surfaces when the jaws are in the closed position;
   said jaw surfaces defining a gap therebetween when said jaws are in the closed position, said gap sized so to minimize damage to tissue captured between the jaw surfaces;
   said jaw surfaces having portions which contact the tissue, said portions having curved surface portions with a minimum radius of curvature chosen to minimize tissue damage when the jaws are in the closed position;
   a suturing needle having a point at a distal end thereof, a handle at a proximal end thereof and a suture exit adjacent the point, said needle adapted to carry a length of suture material along the length of the needle with the distal end of the length of suture material extending past the suture exit;
   the needle having a lateral dimension less than the lateral distance between two adjacent peaks on the first and second jaws when the jaws are in the closed position;
   the jaw surfaces each including an axially extending groove formed therein, the grooves sized to accept the proximal end of the needle when the jaws are in the closed position; and
   the needle being mountable to the body for reciprocal movement along a distal/proximal path between a retracted position, with the needle point located between the proximal end of the body and the axial groove, and an extended position, with the needle housed within said axial groove;
   whereby movement of the needle from the retracted position to the extended position after the tissue has been captured between the jaw surfaces with the jaws in the closed position causes the needle and the length of suture material therewith to pass through the tissue, whereupon movement of the needle from the extended position to the retracted position while preventing the distal end of the suture material from pulling back through the tissue create a pursestring type of suture in the tissue.

22. An improved endoscopic tissue manipulator of the type having user-manipulatable jaws movable between open and closed positions, the improvement comprising:
   the jaws having opposed jaw surfaces, the opposed jaw surfaces being surfaces with troughs and peaks, said jaw surfaces configured so that one or more peaks of said jaw surfaces nest within one or more troughs of the opposed jaw surfaces when the jaws are in the closed position;
   said jaw surfaces defining a gap therebetween when said jaws are in the closed position, said gap sized so to minimize damage to tissue captured between the jaw surfaces;
   said jaw surfaces having portions which contact the tissue, said portions having curved surface portions with a minimum radius of curvature chosen to minimize tissue damage when the jaws are in the closed position; and a needle having a hollow interior and a suture exit defining a pathway from the hollow interior to a region external of the needle.

23. An improved endoscopic device of the type having user manipulatable jaws, the improvement comprising:
   the jaws having opposed jaw surfaces, the opposed jaw surfaces being complementary surfaces with troughs and peaks, said jaw surfaces configured so that one or more peaks of said jaw surfaces nest within one or more troughs of the opposed jaw surfaces when the jaws are in the closed position;
   said jaw surfaces defining a gap therebetween when said jaws are in the closed position, said gap sized so to minimize damage to tissue captured between the jaw surfaces;
   said jaw surfaces being configured to create a plurality of accordion-like folds of said tissue;
   a suturing needle having a point at a distal end thereof, a handle at a proximal end thereof and a suture exit adjacent the point, said needle adapted to carry a length of suture material along the length of the needle with the distal end of the length of suture material extending past the suture exit;
   the needle having a lateral dimension less than the lateral distance between two adjacent peaks on the first and second jaws when the jaws are in the closed position;
   the jaw surfaces each including an axially extending groove formed therein, the grooves sized to accept the proximal end of the needle when the jaws are in the closed position; and
   the needle being mountable to the body for reciprocal movement along a distal/proximal path between a retracted position, with the needle point located between the proximal end of the body and the axial groove, and an extended position, with the needle housed within said axial groove;
   whereby movement of the needle from the retracted position to the extended position after the tissue has been captured between the jaw surfaces with the jaws in the closed position causes the needle and the length of suture material therewith to pass through the tissue, whereupon movement of the needle from the extended position to the retracted position while preventing the distal end of the suture material from pulling back through the tissue create a pursestring type of suture in the tissue.

24. A method for making a pursestring-type of suture using an endoscopic device comprising the following steps:
   selecting jaws for the endoscopic device having opposed jaw surfaces with troughs and peaks which mate when the jaws are in a closed position while leaving a gap between said surfaces sufficient to minimize tissue damage;
   grasping the tissue to be sutured between jaws of the device; thereby creating accordion-like folds in said tissue between said opposed jaw surfaces;
   passing a suture-material-carrying needle through the folds of the tissue while the jaws are in the closed position;
   removing the needle from the tissue while preventing the suture material from passing back through the tissue as the needle is removed;
   releasing the tissue from between the jaws; and
   tying off the suture material to complete the pursestring suture.

25. The method of claim 24 wherein the releasing step occurs before the tying off step.

* * * * *